(12) United States Patent
Komoda

(10) Patent No.: US 10,966,651 B2
(45) Date of Patent: Apr. 6, 2021

(54) ANALYTICS AND PROCESSING OF BIOLOGICAL SIGNALS FROM SENSORS

(71) Applicant: JINS HOLDINGS INC., Maebashi (JP)

(72) Inventor: Taiki Komoda, Gunma (JP)

(73) Assignee: JINS HOLDINGS Inc., Maebashi (JP)

( * ) Notice: Subject to any disclaimer, the term of this patent is extended or adjusted under 35 U.S.C. 154(b) by 430 days.

(21) Appl. No.: 15/775,228

(22) PCT Filed: Nov. 12, 2015

(86) PCT No.: PCT/JP2015/081865
§ 371 (c)(1),
(2) Date: May 10, 2018

(87) PCT Pub. No.: WO2017/081793
PCT Pub. Date: May 18, 2017

(65) Prior Publication Data
US 2018/0344196 A1    Dec. 6, 2018

(51) Int. Cl.
*A61B 5/398*    (2021.01)
*A61B 3/10*    (2006.01)
(Continued)

(52) U.S. Cl.
CPC ............... *A61B 5/398* (2021.01); *A61B 3/10* (2013.01); *A61B 3/113* (2013.01); *A61B 5/6803* (2013.01);
(Continued)

(58) Field of Classification Search
None
See application file for complete search history.

(56) References Cited

U.S. PATENT DOCUMENTS

| 6,431,705 B1 * | 8/2002 | Linden ................... G02C 11/00 351/158 |
| 2004/0070729 A1 | 4/2004 | Wiebe et al. |
| 2008/0294218 A1 | 11/2008 | Savage et al. |

FOREIGN PATENT DOCUMENTS

| EP | 1 871 470 A2 | 1/2008 |
| JP | 2008-534165 A | 8/2008 |

(Continued)

OTHER PUBLICATIONS

International Search Report and Written Opinion for International Application No. PCT/JP2015/081865, dated Feb. 9, 2016.
(Continued)

*Primary Examiner* — G Steven Vanni
(74) *Attorney, Agent, or Firm* — Wolf, Greenfield & Sacks, P.C.

(57) ABSTRACT

An information processing method is executed by a computer having a control unit, wherein the control unit executes: acquiring a plurality of biological signals; detecting for each predetermined time unit a peak part of the respective biological signals; attaching identical identification information to one or a plurality of peak parts forming an identical peak when attaching peak identification information to each of the biological signals; and extracting a combination of corresponding peaks from at least two biological signals on the basis of the identification information of each time unit of the at least two biological signals.

8 Claims, 14 Drawing Sheets

(51) Int. Cl.
    *A61B 3/113*    (2006.01)
    *A61B 5/00*     (2006.01)
    *A61B 5/11*     (2006.01)
    *A61B 5/389*    (2021.01)
(52) U.S. Cl.
    CPC ............ *A61B 5/1103* (2013.01); *A61B 5/389* (2021.01); *A61B 5/4809* (2013.01); *A61B 2503/20* (2013.01)

(56) References Cited

FOREIGN PATENT DOCUMENTS

| JP | 2012-239748 A | 12/2012 |
| JP | 2014-124308 A | 7/2014 |
| WO | WO 2006/105474 A2 | 10/2006 |

OTHER PUBLICATIONS

International Preliminary Report on Patentability for International Application No. PCT/JP2015/081865, dated May 24, 2018.

\* cited by examiner

FIG.10

|   | ChA Signal | ChB Signal | ChC Signal | ChA peakID | ChB peakID | ChC peakID |
|---|---|---|---|---|---|---|
| 1 | 12 | 4 | 63 |  |  | 1C |
| 2 | 33 | 5 | 27 | 1A |  | 1C |
| 3 | 26 | 33 | 12 | 1A | 1B |  |
| 4 | 6 | 7 | 33 |  |  | 2C |
| 5 | 64 | 42 | 2 | 2A | 2B |  |
| 6 | 54 | 33 | 52 | 2A | 2B | 3C |

FIG.11A

| ChA Signal max | ChA peakID | ChB peakID | ChC peakID |
|---|---|---|---|
| 33 | 1A | 1B | 1C |
| 64 | 2A | 2B | 3C |

FIG.11B

| ChB Signal max | ChB peakID | ChA peakID | ChC peakID |
|---|---|---|---|
| 33 | 1B | 1A | |
| 42 | 2B | 2A | 3C |

FIG.11C

| ChC Signal max | ChC peakID | ChA peakID | ChB peakID |
|---|---|---|---|
| 63 | 1C | 1A | |
| 33 | 2C | | |
| 52 | 3C | 2A | 2B |

FIG. 12

| STANDARD DATA AMOUNT OF BIOSENSING | | | | |
|---|---|---|---|---|
| DATA SECTION | 300 SECONDS | | | |
| RESOLUTION | 200Hz | | | |
| INCLUDED PEAKS | 400 PEAKS | | | |
| CHANNELS | 3 CHANNELS | | | |
| INTERVAL FOR DETERMINING IDENTICAL PEAK | 0.1sec | | | |
| ↓ | | | | |
| AMOUNT OF DATA USED IN CALCULATION | NUMBER OF DATA ROWS | | NUMBER OF TABLES | |
| SENSOR DATA (A) | 60,000 | | 1 | |
| PEAK EXTRACTION DATA (B) PER CHANNEL | 400 | | 3 | |
| | | | | |
| PROCESSING SEQUENCE | | | | |
| FOR SENSOR DATA | | 60,000 | LOOPS | |
| Perform PEAK SURPASSING DETERMINATION | | | 1 CONDITIONAL BRANCH | |
| SUM FOR EACH PEAK | | 60,000 | | |
| ↓ | | | | |
| FOR PEAK SURPASSING DETERMINATION RESULT | | 60,000 | | |
| PERFORM EXTRACTING/AGGREGATING OPERATION ON FEATURE POINTS OF EACH PEAK | | 0.5 | | ARITHMETIC LOAD (HALF PROCESSING LOAD OF CONDITIONAL BRANCH IS SUFFICIENT) |
| SUM FOR EACH PEAK | | 30,000 | | |
| SEQ 1 (EXECUTING ABOVE ON EACH CHANNEL) | | 270,000 | | |
| ↓ | | | | |
| DETERMINING FROM PEAK OF A CERTAIN CHANNEL | | 400 | LOOPS | |
| WHETHER OR NOT PEAK OF A CERTAIN CHANNEL GENERATED BY AN IDENTICAL EVENT | | 800 | | ARITHMETIC LOAD (TWICE THE CONDITIONAL BRANCH IN ACCORDANCE WITH RANGE) *NUMBER OF PEAKS OF PARTNER |
| COMBINING | | $2(n-1)!$ | | |
| SEQ 2 SUM | | 640,000 | | |
| | | | | |
| SUM | | 910,000 | | |

FIG. 13

| PROCESSING SEQUENCE | | | |
|---|---|---|---|
| FOR SENSOR DATA | | | |
| EXECUTING PEAK SURPASSING DETERMINATION ON EACH CHANNEL | | | |
| SEQ1 | 60,000 | LOOPS | |
| | 3 | CONDITIONAL BRANCH × 3 | |
| | 180,000 | | |
| FOR PEAK SURPASSING DETERMINATION RESULT | | | |
| PERFORM EXTRACTING/AGGREGATING OPERATION ON FEATURE POINTS OF EACH PEAK | 60,000 | | |
| | 1.0 | ARITHMETIC LOAD (HALF THE PROCESSING LOAD OF CONDITIONAL BRANCH IS SUFFICIENT) × 2 (NOT PURELY THREE TIMES) | |
| SEQ 2 (EXECUTING ABOVE ON EACH CHANNEL) | 180,000 | | |
| SUM | 360,000 | | |

ANALYTICS AND PROCESSING OF BIOLOGICAL SIGNALS FROM SENSORS

CROSS-REFERENCE TO RELATED APPLICATIONS

This Application is a National Stage filing under 35 U.S.C. 371 of International Patent Application Serial No. PCT/JP2015/081865 and entitled "Information Processing Method, Information Processing Device, Program, and Eyewear," filed on Nov. 12, 2015, the contents of which is incorporated herein by reference in its entirety.

TECHNICAL FIELD

The present invention relates to an information processing method, an information processing device, a program, and eyewear.

BACKGROUND ART

Eyewear in which a plurality of electrodes are provided on a frame part and an eye potential signal is acquired from each electrode is available in the prior art (see Patent Document 1, for example).

CITATION LIST

Patent Document

Patent Document 1: U.S. Patent Application Publication No. 2004/0070729 (Specification)

SUMMARY

Technical Problem

Here, when a plurality of signals are acquired, as in the prior art, corresponding peaks may be extracted from the plurality of signals. For example, as a method for checking whether or not the peaks of the respective signals are based on an identical event, a method of extracting corresponding peaks by comparing generation times of the peaks may be used.

In this case, as a general method, a peak value of each signal is determined for the plurality of signals, a combination of any two of the plurality of signals is determined, and corresponding peaks are extracted on the basis of whether or not a time difference between the respective peak values of the two signals is within a predetermined time. According to this method, however, as a number n of determination subject signals increases, the number of combinations of any two signals increases by (n−1)!, leading to a large increase in processing cost, such as required amounts of memory and calculation. It is therefore necessary to reduce the processing cost when extracting corresponding peaks from a plurality of signals.

Hence, an object of the technique disclosed herein is to achieve a reduction in processing cost when extracting corresponding peaks from a plurality of signals.

Solution to Problem

An information processing method according to an aspect of the technique disclosed herein is executed by a computer having a control unit, wherein the control unit executes: acquiring a plurality of biological signals; detecting for each predetermined time unit a peak part of the biological signals; attaching identical identification information to one or a plurality of peak parts forming an identical peak when attaching peak identification information to each of the biological signals; and extracting a combination of corresponding peaks from at least two biological signals on the basis of the identification information of each time unit of the at least two biological signals.

Advantageous Effects of Invention

According to the technique disclosed herein, a reduction in processing cost can be achieved when extracting corresponding peaks from a plurality of signals.

BRIEF DESCRIPTION OF DRAWINGS

FIG. 10 is a view showing examples of three biological signals and identification information attached to each signal.

FIG. 11A is a view showing a result acquired when the identification information of another signal is extracted using the identification information of a signal A as a reference.

FIG. 11B is a view showing a result acquired when the identification information of another signal is extracted using the identification information of a signal B as a reference.

FIG. 11C is a view showing a result acquired when the identification information of another signal is extracted using the identification information of a signal C as a reference.

FIG. 12 is a view illustrating an example of the processing cost of a comparative example.

FIG. 13 is a view illustrating an example of the processing cost of this embodiment.

DESCRIPTION OF EMBODIMENTS

Figure 1:
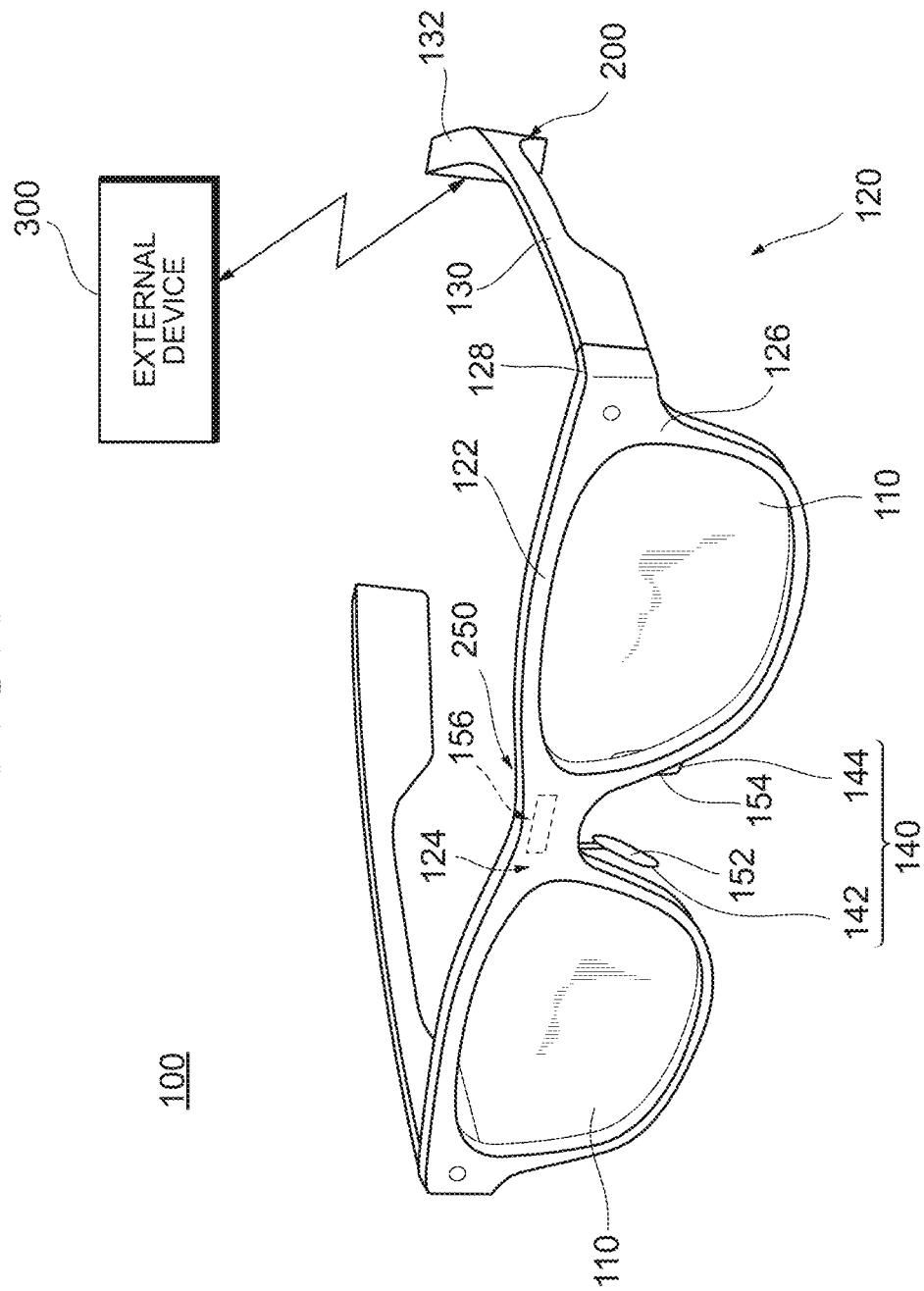
FIG. 1 is a perspective view showing an example of spectacles according to an embodiment from the front.

An embodiment of the present invention will be described below with reference to the figures. Note, however, that the embodiment to be described below is merely an example, and is not intended to exclude various amendments and technical applications not described explicitly below. In other words, the present invention may be implemented after undergoing various amendments within a scope not departing from the spirit thereof. Further, in the following description of the figures, identical or similar parts have been allocated identical or similar reference numerals. The figures are schematic, and do not necessarily reflect actual dimensions, ratios, and so on. Moreover, dimensional relationships and ratios of identical parts may differ between the figures.

Embodiment

Figure 2:
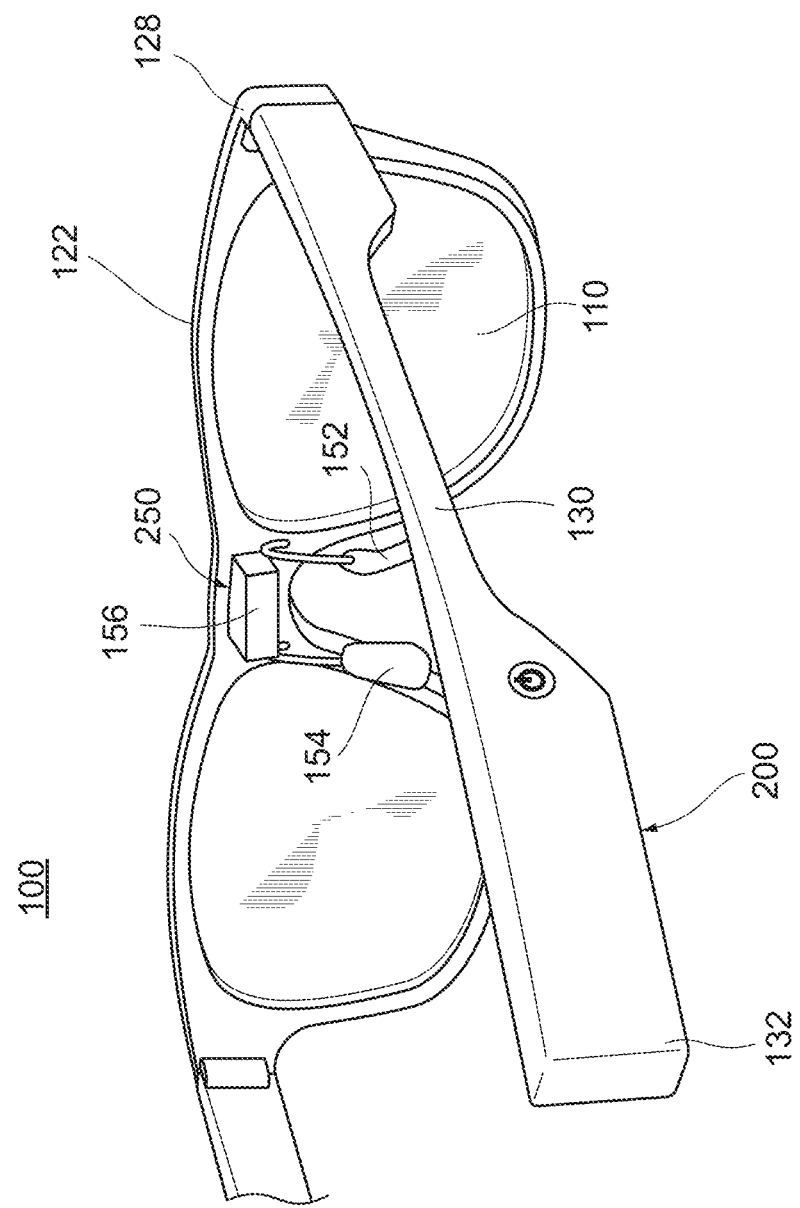
FIG. 2 is a perspective view showing an example of the spectacles according to this embodiment from the rear.

In this embodiment, an eye potential signal is used as an example of a biological signal, and a pair of nose pads provided on spectacles are used as an example of electrode positions in which theoretically similar signals can be measured. FIG. 1 is a perspective view showing an example of spectacles 100 according to this embodiment from the front. FIG. 2 is a perspective view showing an example of the spectacles 100 according to this embodiment from the rear. The spectacles 100 include lenses 110 and a frame 120. The spectacles 100 and the frame 120 serve as an example of eyewear.

The frame 120 supports the pair of lenses 110. The frame 120 includes rims 122, an inter-brow portion (a bridge, for example) 124, end pieces 126, hinges 128, temples 130, temple tips 132, a pair of nose pads 140, a first electrode 152, a second electrode 154, a third electrode 156, electrical wires (not shown), a processing device 200, and an amplification unit 250. Note that depending on the type of the spectacles 100, a single lens may be used so that the bridge part of the frame is omitted. In this case, an inter-brow portion of the single lens serves as the inter-brow portion.

The pair of nose pads 140 include a right nose pad 142 and a left nose pad 144. The rims 122, the end pieces 126, the hinges 128, the temples 130, and the temple tips 132 are each provided in a left-right pair.

The rims 122 hold the lenses 110. The end pieces 126 are provided on respective outer sides of the rims 122 and hold the temples 130 so that the temples 130 can rotate about the hinges 128. The temples 130 press against upper portions of the ears of a user such that the corresponding site is sandwiched between the temples 130. The temple tips 132 are provided on respective tip ends of the temples 130. The temple tips 132 contact the upper portions of the ears of the user. Note that the temple tips 132 do not necessarily have to be provided on the spectacles 100.

The first electrode 152 and the second electrode 154 are provided on respective surfaces of the pair of nose pads 140 in order to detect eye potentials. For example, the first electrode 152 is provided on the right nose pad 142 and the second electrode 154 is provided on the left nose pad 144.

The first electrode 152 detects the eye potential of the right eye of the user. The second electrode 154 detects the eye potential of the left eye of the user. Hence, electrodes for detecting eye potentials are provided on the surfaces of nose pads that naturally contact the skin of the user. As a result, a load exerted on the skin of the user can be lightened in comparison with a case where two pairs of electrodes are brought into contact with the periphery of the eyes of the user.

The third electrode 156 is provided on a surface of the inter-brow portion 124 in order to detect an eye potential. A ground electrode (not shown) does not have to be provided, but may be provided on a surface of the temple tip 132. When the temple tips 132 are not provided on the spectacles 100, a ground electrode is provided on the end of the temple 130. In this embodiment, the potentials detected by the first electrode 152, the second electrode 154, and the third electrode 156 may be based on a potential detected by the ground electrode.

The processing device 200 may be provided on the temple 130, for example. In so doing, the design of the spectacles 100 when seen from the front is not impaired. The processing device 200 does not necessarily have to be disposed on the temple 130, and may be positioned as desired in consideration of balance when the spectacles 100 are worn. The processing device 200 is connected to the amplification unit 250 by an electrical wire. Note that the processing device 200 and the amplification unit 250 may be connected to each other wirelessly.

The amplification unit 250 is provided near the first electrode 152, the second electrode 154, and the third electrode 156, and connected by electrical wires to the respective amplification subject electrodes. The amplification unit 250 acquires eye potential signals indicating eye potentials detected by the electrodes. For example, the amplification unit 250 amplifies eye potential signals indicating the eye potentials detected by the first electrode 152, the second electrode 154, and the third electrode 156.

Further, by providing the amplification unit 250 with a processing unit for executing arithmetic operations on the eye potential signals, the amplification unit 250 may also execute addition/subtraction processing on the respective eye potential signals before or after amplifying the eye potential signals. For example, the amplification unit 250 may determine a reference eye potential signal indicating the potential of the first electrode 152 based on the third electrode 156. Moreover, the amplification unit 250 may determine a reference eye potential signal indicating the potential of the second electrode 154 based on the third electrode 156. Signals amplified or processed by the amplification unit 250 are output to the processing device 200.

The external device 300 is an information processing device having a communication function. For example, the external device 300 is a portable communication terminal such as a mobile telephone or a smartphone carried by the user, a personal computer, or the like. The external device 300 executes processing based on eye potential signals received from a transmission unit 204 shown in FIG. 3. For example, the external device 300 detects blinks or eye movement from the received eye potential signals. As a response issued in a case where blinks are detected, the external device 300 issues a warning to prevent falling asleep on the job after detecting that the number of times the user blinks has increased or the like. The external device 300 will be described in detail below. The external device 300 may also be made capable of operating an application on the basis of detected eye movements. Furthermore, in a case where the processing device 200 makes a predetermined determination based on the eye potential signals, the external device 300 may acquire the determination result from the processing device 200 and execute processing based on the determination result. The predetermined determination is a blink, an eye movement, or the like, for example.

<Configuration of Processing Device 200>

Figure 3:
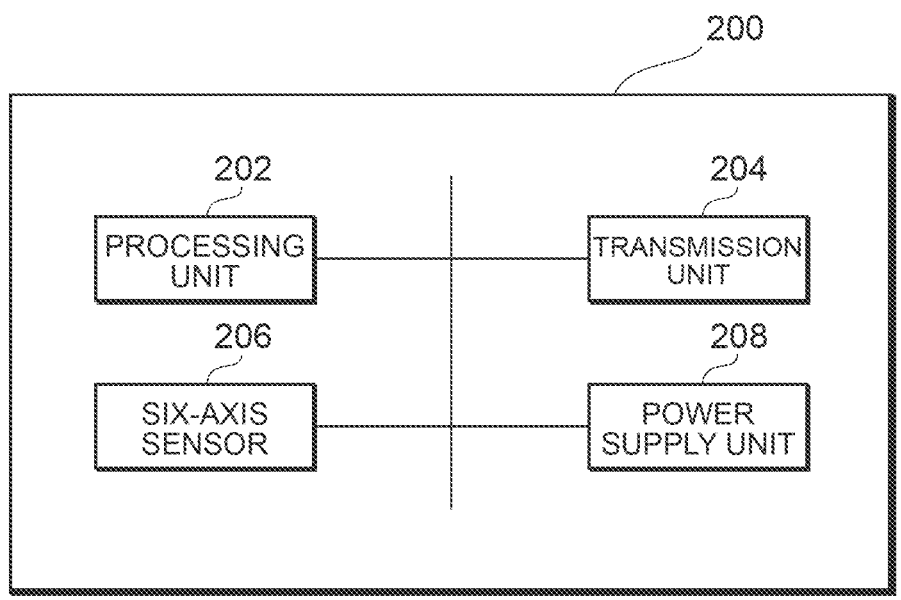
FIG. 3 is a block diagram showing an example of a processing device according to this embodiment.

FIG. 3 is a block diagram showing an example configuration of the processing device 200 according to this embodiment. As shown in FIG. 3, the processing device 200 includes a processing unit 202, the transmission unit 204, a six-axis sensor 206, and a power supply unit 208. Further, bioelectrodes 31, 33, 35 are connected to the processing unit 202 via an amplification unit, for example, using electrical wires. Note that the respective parts of the processing device 200 may be dispersed between the pair of temples instead of being provided on one temple.

The six-axis sensor 206 is constituted by a triaxial acceleration sensor and a triaxial angular velocity sensor. The respective sensors may be provided separately. The six-axis sensor 206 outputs a detected sensor signal (also referred to as detection data) to the processing unit 202.

The processing unit 202 includes a processor and a memory, for example, in order to acquire and process the amplified eye potential signals from the amplification unit 250. For example, the processing unit 202 may process a reference eye potential signal indicating the potential of the first electrode 152 based on the third electrode 156. Note that the term "reference eye potential signal" includes the word "reference" for ease of description, but as a concept, it is included in an eye potential signal. The processing unit 202 may also process a reference eye potential signal indicating the potential of the second electrode 154 based on the third electrode 156.

At this time, the processing unit 202 may execute processing on the left eye and the right eye such that eye potential signals indicating vertical direction and/or horizontal direction movement of the eyes are acquired on the basis of the eye potentials detected by the respective electrodes. For example, the processing unit 202 may generate a vertical direction eye potential signal by subtracting the potential of the second electrode 154 from the potential of the first electrode 152, and may generate a horizontal direction eye potential signal by calculating an average of the potential of the first electrode 152 and the potential of the second electrode 154.

In addition, when the acquired eye potential signals are not digitized, the processing unit 202 executes digitization processing, and when the amplified eye potential signals are acquired from the respective electrodes, the processing unit 202 executes addition/subtraction processing on the eye potential signals. Furthermore, the processing unit 202 may transmit the eye potential signals acquired from the amplification unit 250 to the transmission unit 204 as is.

Moreover, the processing unit 202 processes sensor signals acquired from the six-axis sensor 206 on the respective axes thereof as required, and outputs the processed sensor signals to the transmission unit 204. For example, the processing unit 202 may acquire sensor signals on the respective axes, and generate a first signal indicating a pitch angle, a second signal indicating a roll angle, and so on as required. The pitch angle denotes forward/rearward shaking of the head, for example, while the roll angle denotes left/right shaking of the head, for example. The pitch angle and the roll angle may be calculated using a conventional technique. Further, the processing unit 202 may subject the sensor signals acquired from the six-axis sensor 206 on the respective axes thereof only to amplification and so on. Note that hereafter, the respective eye potential signals, the sensor signals on the respective axes, signals acquired by processing these signals, and so on will be referred to collectively as biological signals.

The transmission unit 204 transmits the respective biological signals processed by the processing unit 202 to the external device 300. For example, the transmission unit 204 transmits the biological signals to the external device 300 by wireless communication such as Bluetooth (registered trademark) or a wireless LAN, or by wired communication. The power supply unit 208 supplies the processing unit 202, the transmission unit 204, the six-axis sensor 206, and so on with electrical power.

Figure 4:
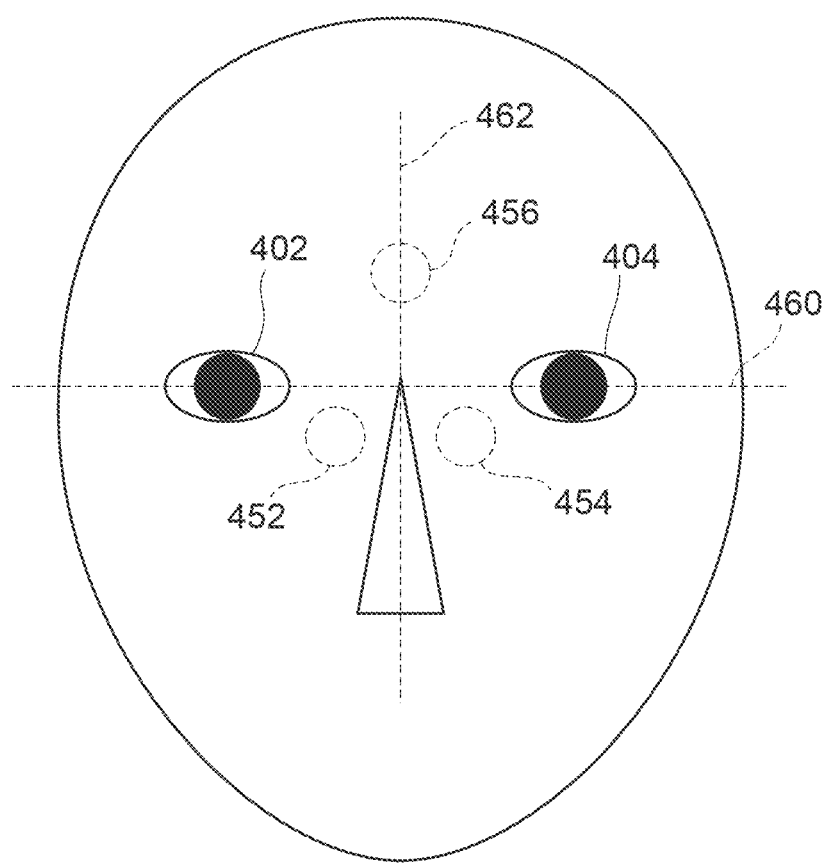
FIG. 4 is a schematic view showing contact positions in which electrodes contact a user.

FIG. 4 is a schematic view showing contact positions in which the electrodes contact the user. A first contact position 452 represents a contact position of the first electrode 152. A second contact position 454 represents a contact position of the second electrode 154. A third contact position 456 represents a contact position of the third electrode 156. A horizontal center line 460 is a horizontal direction center line linking the center of a right eye 402 and the center of a left eye 404. A vertical center line 462 is a center line that intersects the horizontal center line 460 centrally between the right eye 402 and the left eye 404.

The first contact position 452 and the second contact position 454 are preferably positioned on the lower side of the horizontal center line 460. Further, the first contact position 452 and the second contact position 454 are preferably disposed such that a line segment linking respective centers of the first contact position 452 and the second contact position 454 is parallel to the horizontal center line 460.

Furthermore, the first contact position 452 and the second contact position 454 are preferably disposed such that a distance from the first contact position 452 to the right eye 402 is equal to a distance from the second contact position 454 to the left eye 404. Moreover, the first contact position 452 and the second contact position 454 are preferably disposed at least a fixed distance away from each other.

The third contact position 456 is preferably positioned on the vertical center line 462. Further, the third contact position 456 is preferably positioned on the upper side of the horizontal center line 460, away from the first contact position 452 and the second contact position 454. Furthermore, for example, a distance between the third contact position 456 and the right eye 402 may be greater than a distance between the right eye 402 and the first contact position 452, and a distance between the third contact position 456 and the left eye 404 may be greater than a distance between the left eye 404 and the second contact position 454.

In an eyeball, the cornea side is positively charged and the retina side is negatively charged. Therefore, when the eyes move upward, the potential of the first electrode 152 based on the third electrode 156 and the potential of the second electrode 154 based on the third electrode 156 become negative. When the eyes move downward, the potential of the first electrode 152 based on the third electrode 156 and the potential of the second electrode 154 based on the third electrode 156 become positive.

When the eyes move rightward, the potential of the first electrode 152 based on the third electrode 156 becomes negative and the potential of the second electrode 154 based on the third electrode 156 becomes positive. When the eyes move leftward, the potential of the first electrode 152 based on the third electrode 156 becomes positive and the potential of the second electrode 154 based on the third electrode 156 becomes negative.

By detecting the potential of the first electrode 152 based on the third electrode 156 and the potential of the second electrode 154 based on the third electrode 156, the effects of noise can be reduced favorably. To ensure that the third contact position 456 is as far away as possible from the first contact position 452 and the second contact position 454, the inter-brow portion 124 may be disposed on or near an upper end of the rim 122. Further, the third electrode 156 may be provided on the upper side of the center of the inter-brow portion 124. In this case, the wide inter-brow portion 124 is preferably employed as the position for disposing the third electrode 156.

Note that instead of detecting the potential of the first electrode 152 based on the third electrode 156, the processing unit 202 may subtract the potential of the third electrode 156 based on a reference electrode from the potential of the first electrode 152 based on the reference electrode. Similarly, instead of detecting the potential of the second electrode 154 based on the third electrode 156, the processing unit 202 may subtract the potential of the third electrode 156 based on the reference electrode from the potential of the second electrode 154 based on the reference electrode.

The ground electrode may be used as the reference electrode. Alternatively, a reference electrode may be provided on the spectacles 100 separately in a position away from the first electrode 152, second electrode 154, and third electrode 156. For example, the reference electrode may be provided on the right side temple tip 132. The reference electrode may also be provided in a site of the right side temple 130 that contacts the skin of the user.

Note that processing for subtracting the potential of the third electrode 156 from the potential of the first electrode 152 based on the reference electrode and processing for subtracting the potential of the third electrode 156 from the potential of the second electrode 154 based on the reference electrode may be executed by the processing unit 202, the amplification unit 250, or the external device 300. In this case, signals indicating processing subject potentials are amplified by the amplification unit 250.

<Configuration of Amplification Unit>

Figure 5:
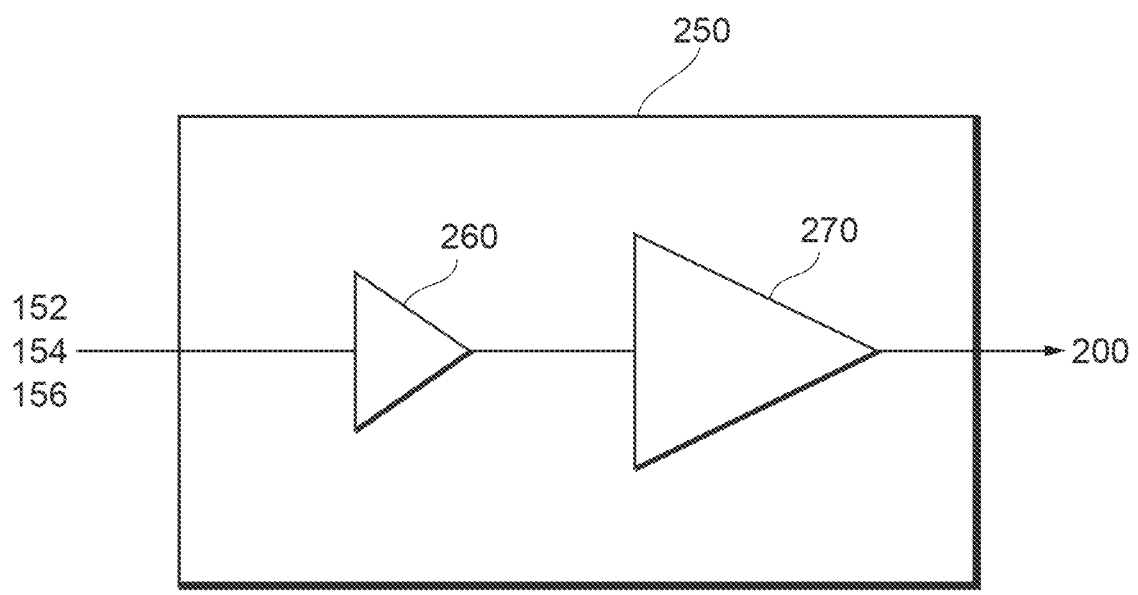
FIG. 5 is a view showing an example configuration of an amplification unit according to this embodiment.

Next, the configuration of the amplification unit 250 will be described. FIG. 5 is a view showing an example configuration of the amplification unit 250 according to this embodiment. As shown in FIG. 5, the amplification unit 250 includes a first amplifier 260 and a second amplifier 270. The first amplifier 260 is positioned in front of the second amplifier 270, and functions as a buffer amplifier. Hereafter, the first amplifier 260 will also be referred to as the buffer amplifier 260. The second amplifier 270 functions as a main amplifier. Hereafter, the second amplifier 270 will also be referred to as the main amplifier 270. Signals amplified by the main amplifier 270 are output to the processing device 200 either by wire or wirelessly.

The amplification unit 250 is preferably disposed in a position on the inter-brow portion 124. Note that the amplification unit 250 may be embedded in the inter-brow portion 124. As described above, the respective electrodes are preferably as far away from each other as possible, but since the positions of the respective electrodes are dependent on the shape of the frame 120, there is a limit to the distances therebetween.

Hence, potential differences between the respective electrodes may not be sufficiently large, and therefore, when noise is intermixed in an eye potential signal indicating a small potential detected by one of the electrodes, it is difficult to detect the potential with a sufficient degree of precision.

In this embodiment, therefore, the amplification unit 250 is provided near the first electrode 152, the second electrode 154, and the third electrode 156 in order to amplify the detected eye potential signals before noise is intermixed therein. For example, the amplification unit 250 is preferably provided on the inter-brow portion 124 part, which is close to the respective electrodes and in which space exists on the frame 120. As a result, the risk of noise becoming intermixed in the eye potential signals detected by the respective electrodes as the signals travel along the electrical wires, leading to a reduction in the precision of the eye potential signals, can be reduced.

Figure 6:
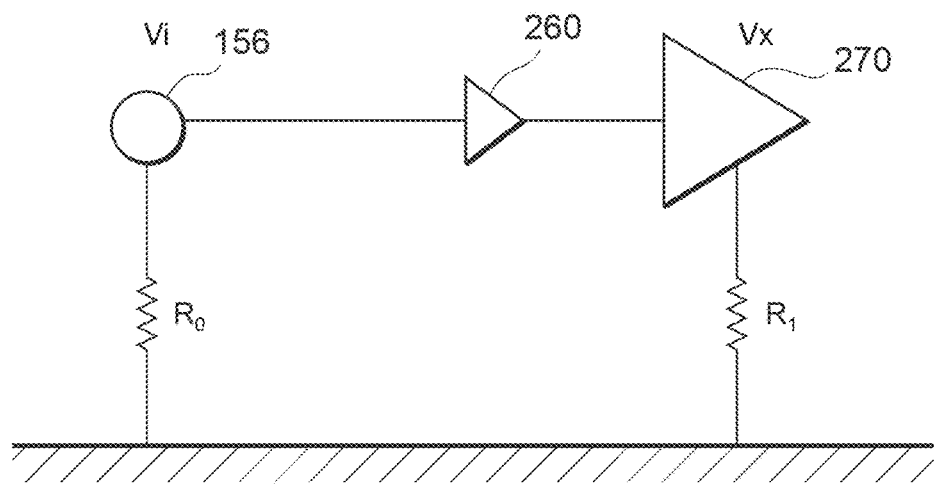
FIG. 6 is a view illustrating a reason for providing a buffer amplifier.

Next, the reason for providing the buffer amplifier 260 in a position in front of the main amplifier 270 will be described using FIG. 6. FIG. 6 is a view illustrating the reason for providing the buffer amplifier 260. In the example shown in FIG. 6, the third electrode 156 is used, but the reason applies similarly to the first electrode 152 and the second electrode 154.

When the spectacles 100 are worn, the third electrode 156 contacts human skin, and therefore resistance (contact resistance) $R_0$ may be assumed to exist relative to the ground. At this time, the contact resistance $R_0$ is several 100 k$\Omega$, for example. Further, internal resistance $R_1$ exists in the main amplifier 270. When a normal amplifier is used as the main amplifier 270 at this time, the internal resistance $R_1$ is between several 10 k$\Omega$ and several 100 k$\Omega$.

Here, ideally, no current flows into the main amplifier 270, but when the internal resistance $R_1$ is smaller than the resistance $R_0$, current flows to the main amplifier 270 side. As a result, a voltage Vi of the electrode and a voltage Vx of the main amplifier 270 are observed as divided voltages. Therefore, the buffer amplifier 260 is provided in a position in front of the main amplifier 270 so that no current flows to the main amplifier 270 side.

Figure 7:
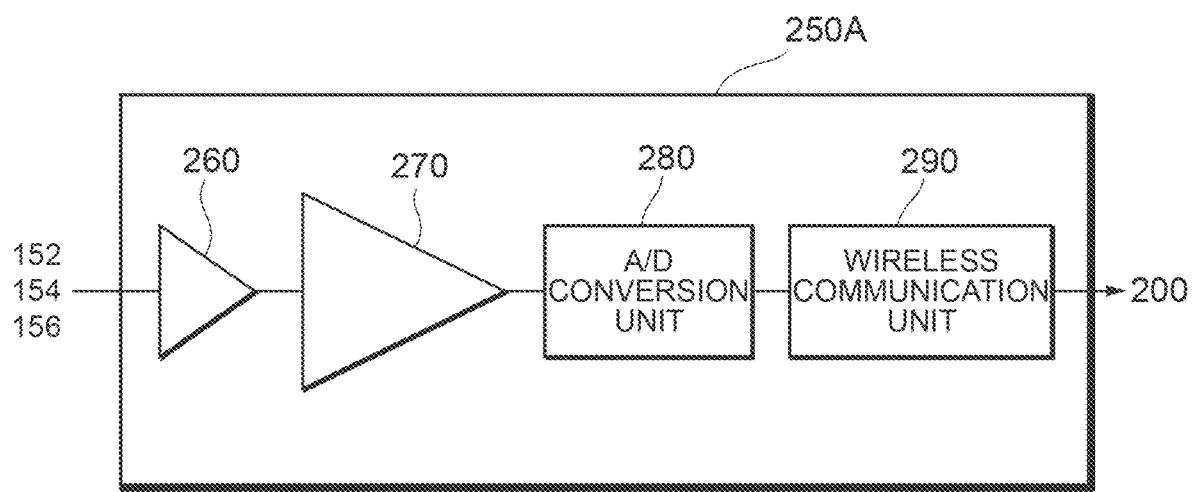
FIG. 7 is a view showing another example configuration of the amplification unit according to this embodiment.

FIG. 7 is a view showing another example configuration of the amplification unit according to this embodiment. The amplification unit shown in FIG. 7 is marked by the reference symbol 250A. The amplification unit 250A includes the buffer amplifier 260, the main amplifier 270, an A/D conversion unit 280, and a wireless communication unit 290. The buffer amplifier 260 and the main amplifier 270 function similarly to those shown in FIG. 5, and therefore the A/D conversion unit 280 and the wireless communication unit 290 will mainly be described below.

The A/D conversion unit 280 converts a signal amplified by the main amplifier 270 from analog to digital. The A/D conversion unit 280 outputs the signal converted to digital to the wireless communication unit 290.

The wireless communication unit 290 transmits the digital signal converted by the A/D conversion unit 280 to the processing device 200 by wireless communication. The wireless communication unit 290 thus functions as a transmission unit. The wireless communication unit 290 uses wireless communication such as Bluetooth (registered trademark) or a wireless LAN, for example. Further, the wireless communication unit 290 may transmit the digital signal directly to the external device 300.

Note that in this embodiment, examples in which the buffer amplifier 260 and the main amplifier 270 are provided singly have been described, and in this case, the eye potential signals from the respective electrodes may be amplified in a sequence determined in advance. Alternatively, the buffer amplifier 260 and the main amplifier 270 may be provided for each electrode.

<Configuration of External Device>

Figure 8:
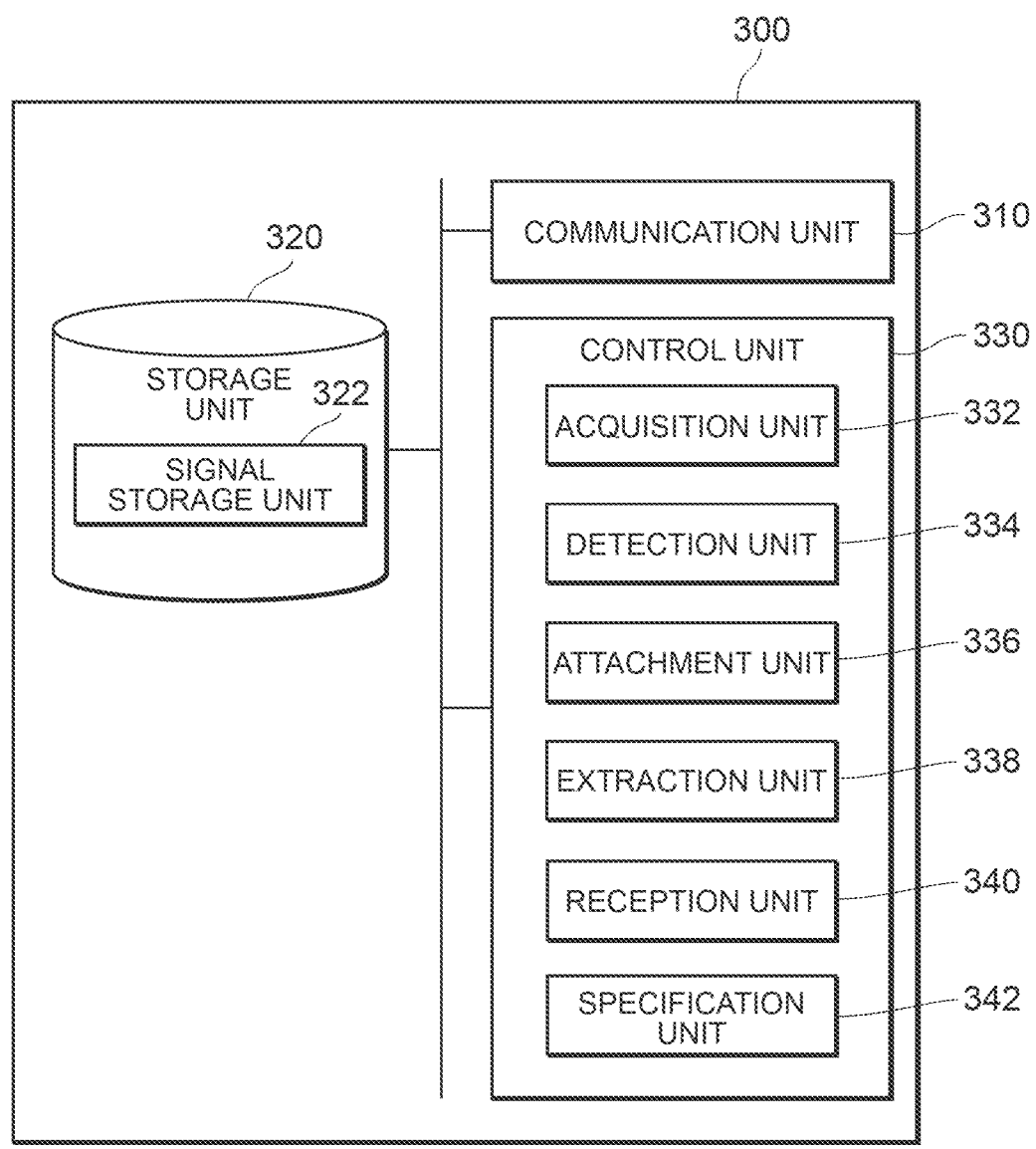
FIG. 8 is a block diagram showing an example configuration of an external device according to this embodiment.

Next, the configuration of the external device 300 will be described. FIG. 8 is a block diagram showing an example configuration of the external device 300 according to this embodiment. As shown in FIG. 8, the external device 300 includes a communication unit 310, a storage unit 320, and a control unit 330.

The communication unit 310 is a communication interface, for example, which receives the respective biological signals and so on either by wireless communication such as Bluetooth (registered trademark) or a wireless LAN, or by wired communication. The communication unit 310 outputs the biological signals and so on received from the transmission unit 204 of the processing device 200 to the storage unit 320 and/or the control unit 330.

The storage unit 320 is a RAM (Random Access Memory) or a ROM (Read Only Memory) that stores data relating to processing of the biological signals and so on, for example. The storage unit 320 includes a signal storage unit 322, for example, and the signal storage unit 322 stores biological signals that are to be and/or have been processed by the control unit 330, such as the eye potential signals of the left and right eyes, the sensor signals, and so on.

The storage unit 320 also stores a program for causing a computer to execute signal processing to be described below. The program may be installed on the external device 300 via the Internet or a recording medium such as an SD card, or may be pre-installed. Alternatively, a storage unit storing the program may be provided separately to the storage unit 320.

The control unit 330 is a CPU (Central Processing Unit), for example, which controls the respective units and executes various types of calculation processing. In the example shown in FIG. 8, the control unit 330 includes at least an acquisition unit 332, a detection unit 334, an attachment unit 336, an extraction unit 338, a reception unit 340, and a specification unit 342.

The acquisition unit 332 acquires a plurality of different biological signals from the storage unit 320 or the communication unit 310. The plurality of different biological signals include eye potential signals based on the eye potentials detected by the respective electrodes contacting the periphery of the eyes of the subject, and the sensor signals acquired from the six-axis sensor 206 on the respective axes thereof. Hereafter, an example in which the acquired eye potential signals are the eye potential signals acquired respectively from the first electrode 152 and the second electrode 154 will be described. Note that the eye potential signals may be eye potential signals acquired respectively from the first electrode 152 and the second electrode 154 using the third electrode 156 or the ground electrode, for example, as a reference. Also note that the respective biological signals include signal values acquired at intervals of a predetermined time unit (a sampling interval).

The detection unit 334 detects for each predetermined time unit a peak part of the biological signals. The "peak part" denotes a peak or a peak periphery including the peak. For example, the detection unit 334 detects peak parts in which the signal value of the biological signal at each sampling timing is not lower than a first threshold and not higher than a second threshold. The first and second thresholds may be set at appropriate values for each biological signal. Note that the detection unit 334 may execute the threshold determinations using absolute values of the biological signals.

Further, the detection unit 334 may determine an extreme value of each biological signal acquired by the acquisition unit 332, and detect peak parts on the basis of the extreme value. For example, the detection unit 334 detects a range of several sampling timings from the extreme value as peak parts. The extreme value may be calculated using a conventional determination method. Further, the detection unit 334 notifies the attachment unit 336 of the detected peak parts.

The attachment unit 336, when attaching peak identification information to each biological signal, attaches identification information indicating an identical peak to one or a plurality of peak parts forming the same peak. Further, the attachment unit 336 attaches different identification information to different peaks. For example, for each biological signal, the attachment unit 336 attaches an identical ID, label, or the like to identical peaks, and attaches a different ID, label, or the like to different peaks. The attachment unit 336 can determine whether or not a peak is identical by, for example, determining whether or not consecutive signal values are not lower than the first threshold, not higher than the second threshold, and so on. More specifically, the attachment unit 336 determines that consecutive peak parts having signal values that are not lower than the first threshold and not higher than the second threshold denote an identical peak.

The extraction unit 338 extracts a combination of corresponding peaks from at least two biological signals on the basis of the identification information of each predetermined time unit of the at least two biological signals. Here, "a combination of corresponding peaks" signifies a combination of peaks that appear to have been generated in different signals on the basis of an identical event, for example.

For example, the extraction unit 338 can extract a combination of corresponding peaks by determining, with respect to the identification information attached to a predetermined biological signal at a certain sampling timing, whether or not identification information is attached to another biological signal at the same sampling timing. In so doing, it is necessary simply to compare correspondence relationships between the identification information identifying the peak parts in each time unit, and therefore the need to determine time differences between the peaks of arbitrary signals and so on, as in the prior art, can be eliminated, leading to a reduction in processing cost. Note that a specific example illustrating a reduction in processing cost will be described below using FIGS. 12 and 13.

The extraction unit 338 may also determine whether or not the respective peak parts of a plurality of biological signals received by the reception unit 340, to be described below, indicate peaks based on an identical event. For example, when identification information is attached to all of the biological signals at the same sampling timing, the extraction unit 338 may determine that the peak parts of the biological signals indicate peaks based on an identical event.

Furthermore, when biological information including a peak part to which identification information is attached exists in a plurality in each time unit, the extraction unit 338 may associate the identification information of the plurality of biological signals and set the associated information as "a combination of corresponding peaks". As a result, a combination of peaks can be expressed using associations between the identification information.

The reception unit 340 receives at least two biological signals designated from among the plurality of biological signals. For example, the reception unit 340 receives at least two biological signals designated by an input device (not shown) provided in the external device 300. The received biological signals are set in the extraction unit 338 as extraction subject biological signals. More specifically, the reception unit 340 may receive the eye potential signal of the right eye and the eye potential signal of the left eye as signals designated from among the plurality of biological signals.

In this case, the extraction unit 338 executes extraction processing on the basis of identification signals of the at least two biological signals received by the reception unit 340. Thus, the user can designate a plurality of biological signals in accordance with the aim of the extraction, and as a result, the extraction processing can be executed on desired biological signals among the plurality of biological signals.

The specification unit 342 specifies one first biological signal from among the at least two biological signals. For example, the specification unit 342 specifies a biological signal to be used as a reference from among the extraction subject biological signals. As regards this specification, the first biological signal may be specified by the user via the reception unit 340, or a single biological signal may be specified automatically from among the extraction subjects. Further, the specified biological signal is not limited to a single biological signal, and the biological signals may be specified one at a time in a predetermined order. Thus, when a biological signal to be used as an extraction reference is determined, the extraction processing can be executed using the biological signal as a reference. For example, when the user runs while wearing the spectacles 100, vertical shaking affects the eye potential signals, and therefore the respective eye potential signals can be compared using a vertical direction sensor signal acquired by the acceleration sensor as a reference.

Further, the extraction unit 338 extracts identification information corresponding to the identification information of the first biological signal from the identification information of another biological signal, among the extraction subject biological signals, that is different to the specified first biological signal. Here, the "identification information corresponding to the identification information of the first biological signal" signifies the identification information of another biological signal attached at the same timing as the sampling timing of the first biological signal to which the identification information is attached.

In this case, the extraction unit 338 executes the processing for extracting corresponding peaks on the basis of an extraction result relating to the extracted identification information. Hence, by comparing peaks using peak parts to which identification information has been attached in advance, a combination of peaks can be extracted easily.

Furthermore, when extracting the identification information, the extraction unit 338 may include a maximum signal value of the signal values of the peak parts within the same peak in the extraction result as a peak value. Hence, in a case where peaks are compared using peak values, the peak value can be obtained easily from the extraction result and used to compare the peak values.

<Specific Example of Peak Value>

Figure 9A:
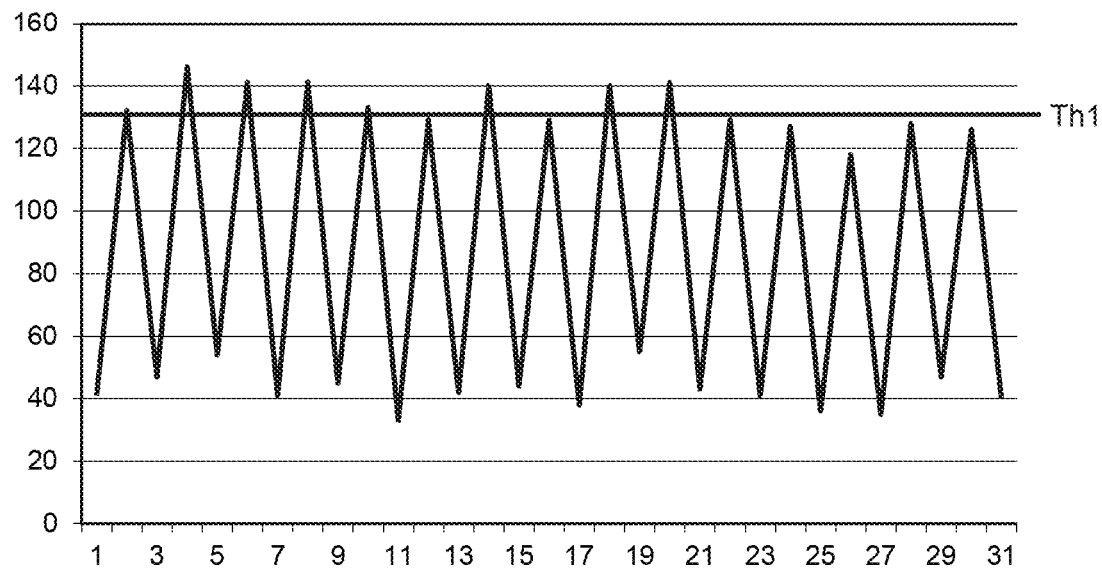
FIG. 9A is a graph showing an example of an eye potential signal of a left eye.
Figure 9B:
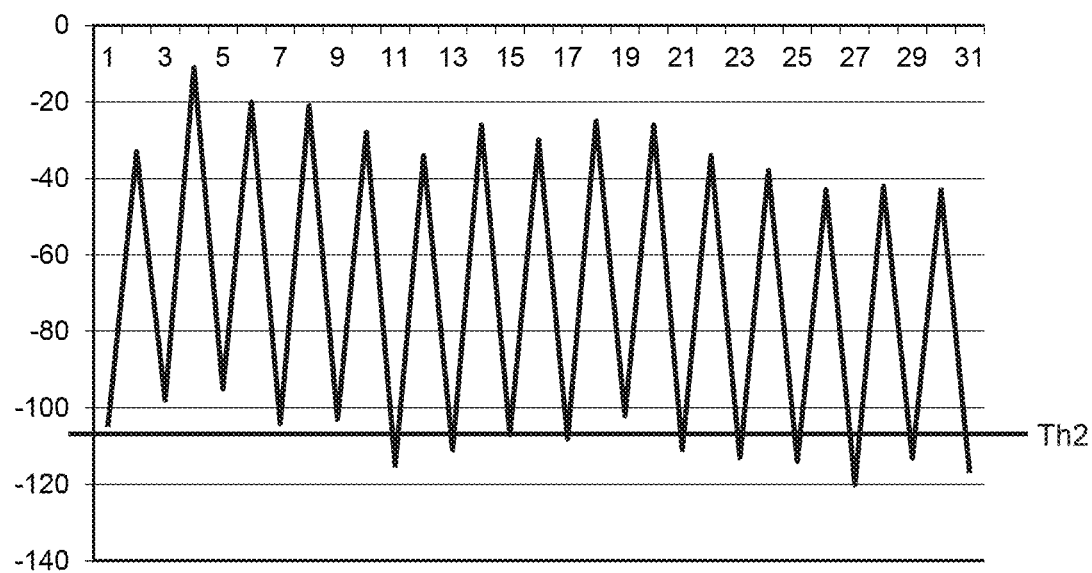
FIG. 9B is a graph showing an example of an eye potential signal of a right eye.
Figure 9C:
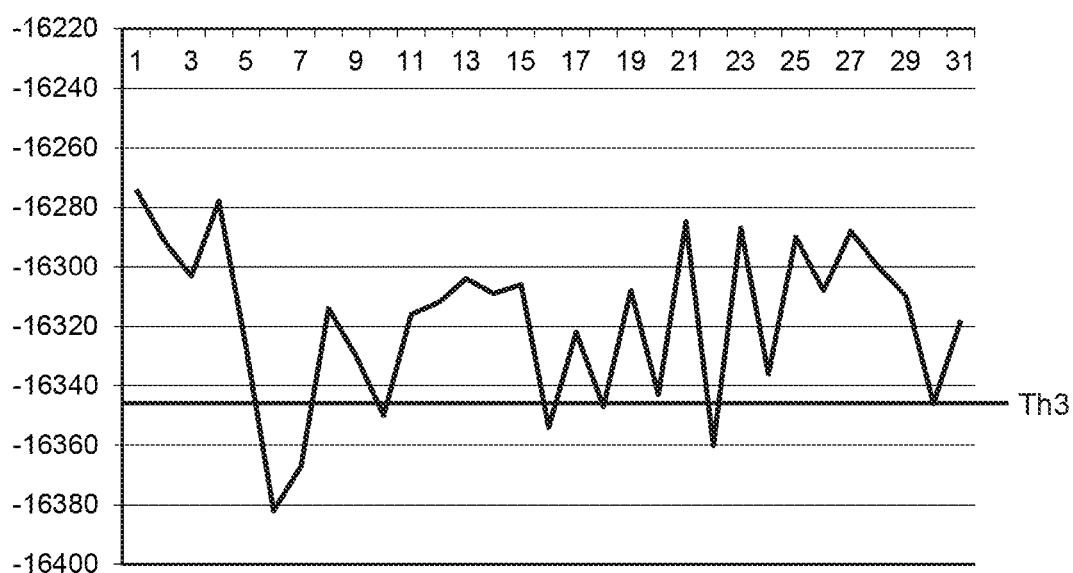
FIG. 9C is a graph showing an example of a sensor signal indicating vertical direction (Z direction) acceleration detected from a six-axis sensor.

FIGS. 9A to 9C show examples of values of biological signals stored in the signal storage unit 322. Note that in the examples shown in FIGS. 9A to 9C, values of biological signals sampled at a predetermined sampling rate are stored. In the examples shown in FIGS. 9A to 9C, the horizontal axis shows time (the sampling timing) and the vertical axis shows signal strength.

FIG. 9A is a graph showing an example of the eye potential signal of the left eye. In the example shown in FIG. 9A, a first threshold Th1 for detecting a predetermined peak part is indicated. In the example shown in FIG. 9A, the detection unit 334 detects signal values of the eye potential signal of the left eye that equal or exceed the first threshold as peak parts, and for each peak, the attachment unit 336 attaches identification information to one or a plurality of peak parts forming the same peak.

FIG. 9B is a graph showing an example of the eye potential signal of the right eye. In the example shown in FIG. 9B, a second threshold Th2 for detecting a predetermined peak part is indicated. In the example shown in FIG. 9B, the detection unit 334 detects signal values of the eye potential signal of the right eye that are equal to or lower than the second threshold as peak parts, and for each peak, the attachment unit 336 attaches identification information to one or a plurality of peak parts forming the same peak.

FIG. 9C is a graph showing an example of a sensor signal indicating vertical direction (Z direction) acceleration detected from the six-axis sensor 206. In the example shown in FIG. 9C, a third threshold Th3 for detecting a predetermined peak part is indicated. In the example shown in FIG. 9C, the detection unit 334 detects signal values of the sensor signal that are equal to or lower than the third threshold as peak parts, and for each peak, the attachment unit 336 attaches identification information to one or a plurality of peak parts forming the same peak.

Note that FIGS. 9A to 9C show examples in which the detection unit 334 uses a single threshold for a single biological signal, but instead, peak parts forming a maximum value and peak parts forming a minimum value may be detected using a plurality of thresholds.

<Example of Stored Data>

Next, using FIGS. 10 and 11, an example in which three biological signals that are different to the biological signals shown in FIGS. 9A and 9C are stored in the signal storage unit 322 together with identification information will be described. FIG. 10 is a view showing an example of the three biological signals and the identification information attached respectively thereto. On a table shown in FIG. 10, the respective biological signals and the respective identification information are listed as items on the first row. For example, a signal A (a ChA Signal), a signal B (a ChB Signal), and a signal C (a ChC Signal) are included as the biological signals, while identification information A (a ChA peakID), identification information B (a ChB peakID), and identification information C (a ChC peakID) are included as the identification information.

On each row of the table shown in FIG. 10, signal values are stored for each sampling timing. For example, at a sampling timing 1, "12", "4", and "63" are stored for the signal A, the signal B, and the signal C, respectively. At this time, the detection unit 334 determines that the value "63" of the signal C exceeds a predetermined threshold, and therefore extracts this signal value as a peak part. Next, the attachment unit 336 associates identification information "1C" with the signal value "63" and attaches the identification information thereto. When similar processing is executed up to a sampling timing 6, the data shown in FIG. 10 are stored in the signal storage unit 322.

FIGS. 11A to 11C are views illustrating extraction results acquired by the extraction unit 338. FIG. 11A is a view showing a result acquired when the identification information of another signal is extracted using the identification information of a signal A as a reference. In the example shown in FIG. 11A, with respect to sampling timings 2 and 3, at which identification information "1A" is attached to the signal A, the extraction unit 338 extracts identification information "1C" of a signal C at the sampling timing 2 and extracts identification information "1 B" of a signal B at the sampling timing 3. The extraction unit 338 then associates the extracted identification information "1 B" and "1C" of the signals B and C as a whole with the identification information "1A". Further, the extraction unit 338 extracts a maximum value "33" of the values of the signal A to which the identification information "1A" is attached, and associates the extracted value with the identification information "1A".

Next, with respect to sampling timings 5 and 6, at which identification information "2A" is attached to the signal A, the extraction unit 338 extracts identification information "2B" of the signal B at the sampling timing 5, and extracts the identification information "2B" of the signal B and identification information "3C" of the signal C at the sampling timing 6. The extraction unit 338 then associates the extracted identification information "2B" and "2C" of the signals B and C as a whole with the identification information "2A". Further, the extraction unit 338 extracts a maximum value "64" of the values of the signal A to which the identification information "2A" is attached, and associates the extracted value with the identification information "2A".

FIG. 11B is a view showing a result acquired when the identification information of another signal is extracted using the identification information of the signal B as a reference. In the example shown in FIG. 11B, the extraction unit 338 extracts identification information "1A" of the signal A at a sampling timing 3, at which identification information "1 B" is attached to the signal B. The extraction unit 338 then associates the extracted identification information "1A" of the signal A with the identification information "1 B". Further, the extraction unit 338 extracts a value "33" of the signal B to which the identification information "1 B" is attached, and associates the extracted value with the identification information "1 B".

Next, with respect to sampling timings 5 and 6, at which identification information "2B" is attached to the signal B, the extraction unit 338 extracts identification information "2A" of the signal A at the sampling timing 5, and extracts the identification information "2A" of the signal A and identification information "3C" of the signal C at the sampling timing 6. The extraction unit 338 then associates the extracted identification information "2A" and "3C" of the signals A and C as a whole with the identification information "2B". Further, the extraction unit 338 extracts a maximum value "42" of the values of the signal B to which the identification information "2B" is attached", and associates the extracted value with the identification information "2B".

FIG. 11C is a view showing a result acquired when the identification information of another signal is extracted using the identification information of the signal C as a reference. In the example shown in FIG. 11C, with respect to sampling timings 1 and 2, at which identification information "1C" is attached to the signal C, the extraction unit 338 extracts identification information "1A" of the signal A at the sampling timing 2. The extraction unit 338 then associates the extracted identification information "1A" of the signal A with the identification information "1C". Further, the extraction unit 338 extracts a value "63" of the signal C to which the identification information "1C" is attached, and associates the extracted value with the identification information "1C".

Next, at a sampling timing 4, at which identification information "2C" is attached to the signal C, no corresponding identification information is attached to the other signals, and therefore the extraction unit 338 does not extract any identification information. Further, the extraction unit 338 extracts a maximum value "33" of the values of the signal C to which the identification information "2C" is attached, and associates the extracted value with the identification information "2C".

Next, the extraction unit 338 extracts the identification information "2A" of the signal A and the identification information "2B" of the signal B at a sampling timing 6, at which identification information "3C" is attached to the signal C. The extraction unit 338 then associates the extracted identification information "2A" and "2B" of the signals A and B as a whole with the identification information "3C". Further, the extraction unit 338 extracts a maximum value "52" of the values of the signal C to which the identification information "3C" is attached, and associates the extracted value with the identification information "3C".

Hence, when identification information is attached to all of the signals at a certain sampling timing on each of the tables showing identification information extraction results, the extraction unit 338 determines that the peak parts of the respective signals corresponding to the identification information denote peaks based on an identical event. Thus, the identification information extraction results can be used to determine whether or not peaks of a plurality of desired signals are based on an identical event and so on easily while achieving a reduction in processing cost.

Note that in order to determine that identification information is attached to all of the signals, the extraction unit 338 may determine that identification information is attached to all of the signals at the same timing from the table shown in FIG. 10. In so doing, the processing cost of the extraction processing can be reduced.

<Example of Reduction in Processing Cost>

Next, the processing cost of a comparative example representing typical peak synchronization processing will be compared with the processing cost of this embodiment. FIG. 12 is a view illustrating an example of the processing cost of the comparative example. Here, "typical peak synchronization processing" is a method of extracting corresponding peaks by (1) executing a threshold determination on each signal, (2) detecting peaks, and (3) finally, determining a time difference between the peaks.

Conditions of the comparative example shown in FIG. 12 are as follows.

Data section: 300 sec
Resolution (sampling number): 200 Hz
Included (detected) peaks: 400
Number of channels (number of signals): 3
Interval for determining identical peak: 0.1 sec (1) Under the above conditions, first, a following calculation amount is required to determine the existence of a peak in a single signal. The calculation amount is denoted as "processing name (or data): calculation cost".

Sensor data: 200 (Hz)×300 (seconds)=60000
Peak surpassing determination (threshold determination):
    1 (assuming that the calculation amount of a conditional branch (whether or not the value equals or exceeds the threshold) is 1)
Sum for each peak: 60000×1=60000

(2) Next, a following calculation amount is required to extract and aggregate feature points of the peaks relating to the determination results indicating peak surpassing (exceeding the threshold).

Processing for determining whether or not a determination result indicating peak surpassing has been acquired: 60000
Extracting and aggregating feature points of each peak:
    0.5 (half the calculation amount of the conditional branch)
Sum for each peak: 60000×0.5=30000
Sum of (1)+(2) for all channels: (60000+30000)×3=270000

(3) Next, a following calculation amount is required to determine whether or not the extracted peaks relate to an identical phenomenon (event).

Number of peaks: 400
Determination as to whether or not one peak relates to an identical event: 800 (the calculation amount is assumed to be 2; calculation amount×number of other peaks=2×400)

Combining with other signals: (n−1)!=2
Sum: 400×800×2=640000

Hence, the total calculation amount of the comparative example is (the sum of (1)+(2) for all channels)+(3), which corresponds to 270000+640000=910000. Here, when the method of the comparative example is used, as the number of signals n increases, the number of combinations (n−1)! becomes extremely large.

FIG. 13 is a view illustrating an example of the processing cost of this embodiment. The conditions of the embodiment shown in FIG. 13 are identical to the conditions shown in FIG. 12.

(1) Under the above conditions, first, a following calculation amount is required to determine the existence of a peak part in a single signal.
Sensor data: 200 (Hz)×300 (seconds)=60000
Peak surpassing determination for respective channels: 3 (conditional branch×3=1×3)
Sum: 60000×3=180000

(2) Next, a following calculation amount is required to extract and aggregate feature points of the peaks relating to the determination results indicating peak surpassing (detected as peak parts).
Processing for determining whether or not a determination result indicating peak surpassing has been acquired: 60000
Extracting and aggregating feature points of each peak: 1.0 (0.5 (half the processing load of the conditional branch)×2 (not all channels include corresponding peaks, and therefore 0.5 is not simply multiplied by 3))
Sum for all channels: 60000×1.0×3=180000

Hence, the total calculation amount of this embodiment is (1)+(2), which corresponds to 180000+180000=360000.

It is evident from a comparison of the processing cost (910000) of the comparative example, shown in FIG. 12, and the processing cost (360000) of this embodiment, shown in FIG. 13, that according to this embodiment, the processing cost can be greatly reduced.

<Operation>

Figure 14:
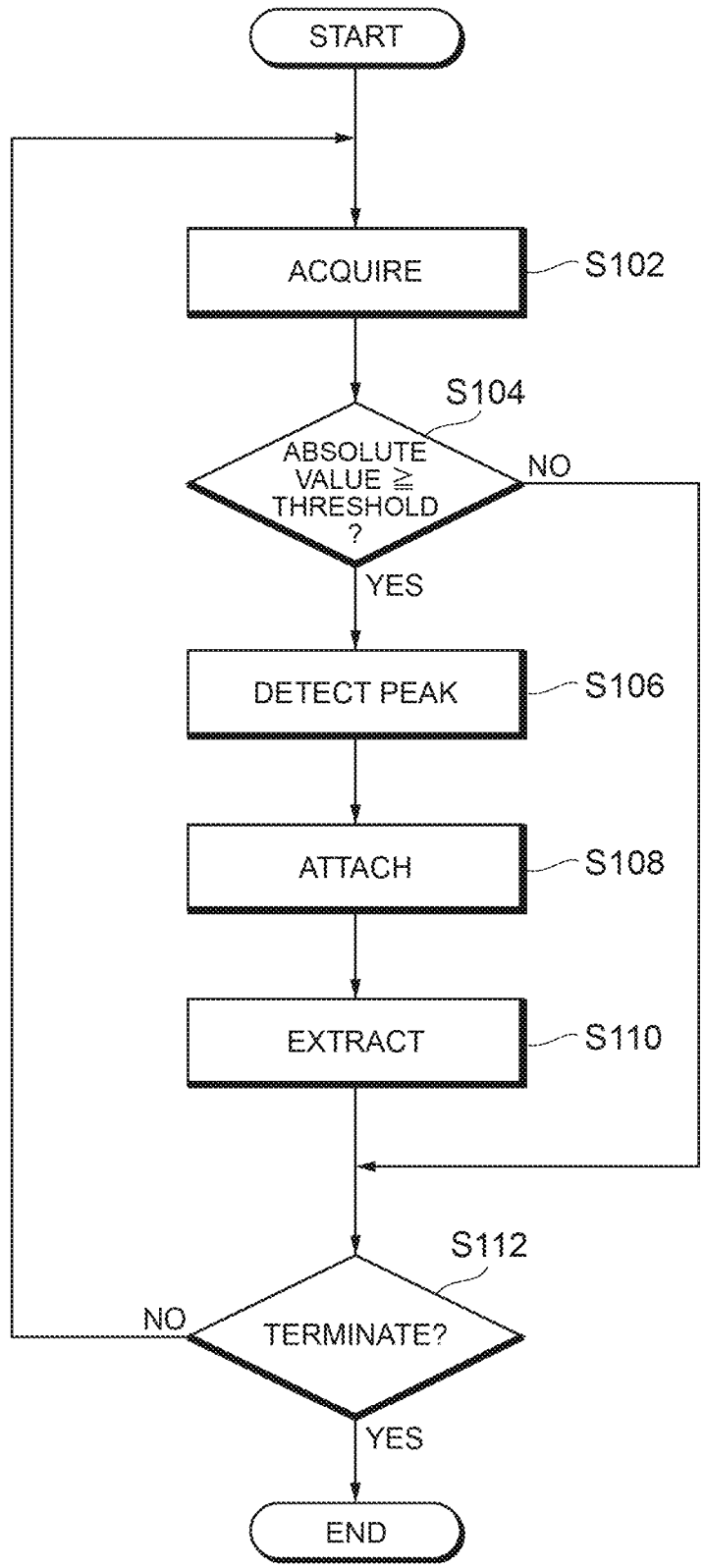
FIG. 14 is a flowchart showing an example of extraction processing A according to this embodiment.

Next, an operation of the external device 300 according to this embodiment will be described. FIG. 14 is a flowchart showing an example of extraction processing A according to this embodiment. The extraction processing A is simple extraction processing executed during the extraction processing described above. The flowchart shown in FIG. 14 is started when the external device 300 is set in an operating mode (a normal mode) serving as a signal acquisition mode in a condition where, for example, the user is wearing the spectacles 100 and the first electrode 152, second electrode 154, and third electrode 156 are in contact with the skin of the user.

In step S102 shown in FIG. 14, the acquisition unit 332 starts to acquire the plurality of biological signals from the spectacles 100.

In step S104, the detection unit 334 determines whether or not the absolute value of each predetermined time unit of the biological signals equals or exceeds a threshold. When the absolute value equals or exceeds the threshold (step S104—YES), the processing advances to step S106, and when the absolute value is lower than the threshold (step S104—NO), the processing advances to step S112.

In step S106, the detection unit 334 detects signal values equaling or exceeding the threshold as peak parts. Note that another method may be used to detect the peak parts.

In step S108, the attachment unit 336 attaches identical identification information to one or a plurality of peak parts forming the same peak for each biological signal. The identification information is information identifying a peak. At this time, the attachment unit 336 attaches different identification information to each different peak.

In step S110, the extraction unit 338 extracts combinations of corresponding peaks from at least two biological signals serving as extraction subjects using the identification information of each time unit of the extraction subject biological signals.

In step S112, the control unit 330 determines whether or not an instruction to terminate the processing has been issued. When a termination instruction has been issued (step S112—YES), the processing is terminated, and when a termination instruction has not been issued (step S112—NO), the processing returns to step S102. Hence, corresponding peaks can be extracted using the identification information, and as a result, a reduction in processing cost can be achieved.

Figure 15:
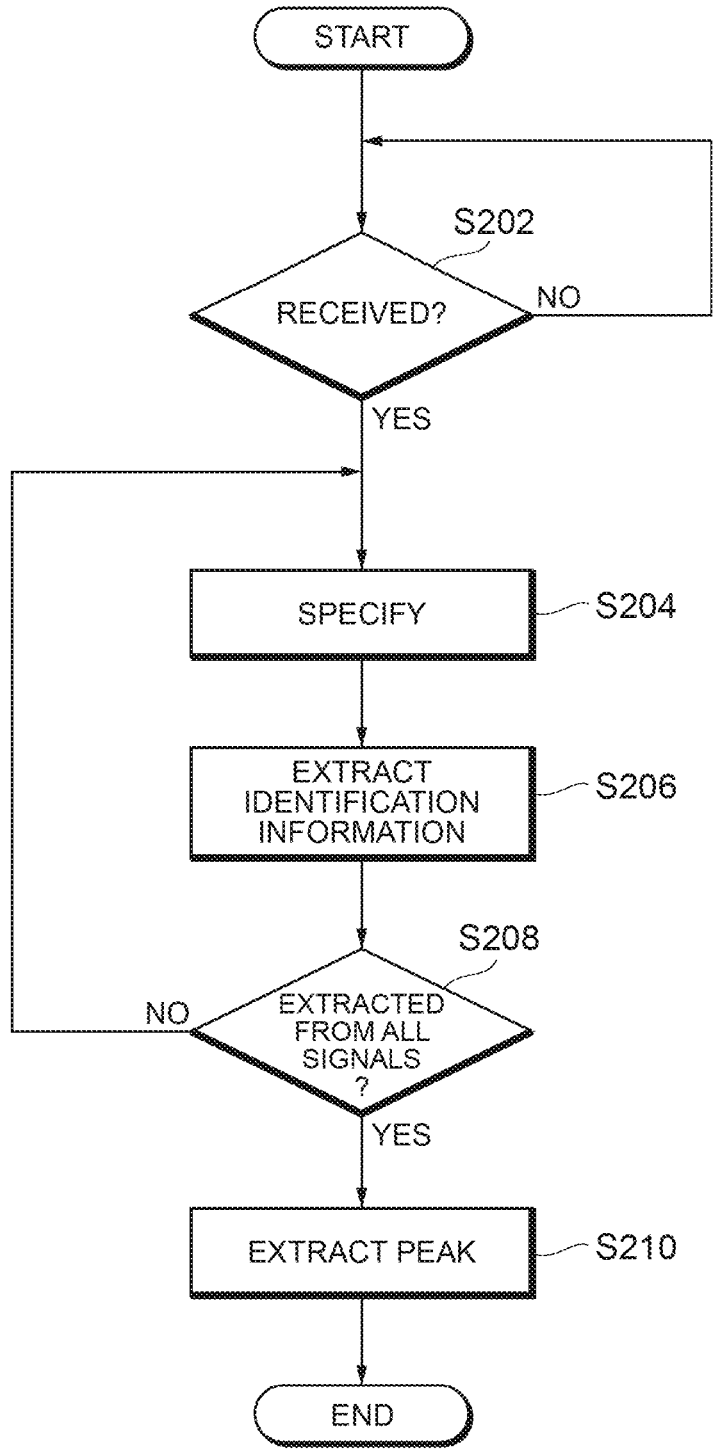
FIG. 15 is a flowchart showing an example of extraction processing B according to this embodiment.

FIG. 15 is a flowchart showing an example of the extraction processing according to this embodiment. In step S202 shown in FIG. 15, the reception unit 340 determines whether or not a designation of at least two biological signals among the plurality of biological signals has been received. When a designation has been received (step S202—YES), the processing advances to step S204, and when a designation has not been received (step S202—NO), the processing returns to step S202.

In step S204, the specification unit 342 specifies one first biological signal from among the at least two biological signals.

In step S206, the extraction unit 338 extracts identification information corresponding to the identification information of the first biological signal from the identification information of the other biological signal or signals among the at least two biological signals.

In step S208, the control unit 330 determines whether or not the extraction processing has been executed on all of the at least two biological signals. When the extraction processing has been executed on all of the biological signals (step S208—YES), the processing advances to step S210, and when the extraction processing has not been executed on all of the biological signals (step S208—NO), the processing advances to step S204, where a different biological signal is specified.

In step S210, the extraction unit 338 executes comparison processing on the basis of the identification information extraction result. In so doing, a combination of corresponding peaks can be extracted by comparing the identification information of a specific biological signal with that of a desired biological signal using the specific biological signal as a reference.

Note that as long as no inconsistencies occur in the processing content, the respective processing steps included in the processing flows illustrated in FIGS. 14 and 15 may be executed in an appropriately modified order or in parallel, and other steps may be added between the respective processing steps. Further, a step described for convenience as a single step may be executed after being divided into a plurality of steps, while steps described for convenience as a plurality of steps may be considered as a single step.

According to the embodiment described above, a reduction in processing cost can be achieved when extracting corresponding peaks from a plurality of signals.

In this embodiment, when corresponding peaks are extracted, subsequent processing may be executed using the peak values of the corresponding peaks. For example, in the eye potential signal of the left eye and the eye potential signal of the right eye, peak values extracted as an identical event may be used in processing for determining blinks, eye movement, and so on.

<Peak Width Determination>

Determination of a peak width will now be described as pre-processing for determining blinks, eye movement, and so on. For example, a peak width determination unit (not shown) specifies a peak width indicating a period during which the peak value of each of the extracted eye potential signals of the left eye and the right eye is not lower than the first threshold and not higher than the second threshold.

<Blink Determination>

Determination of a blink will now be described. For example, a blink determination unit (not shown) determines that a blink has been performed when the respective potentials of the first electrode 152 and the second electrode 154 based on the inter-brow third electrode 156 are negative and in phase, and the peak width is within a predetermined period (0.25 seconds, for example).

<Eye Movement Determination>

Determination of an eye movement will now be described. For example, an eye movement determination unit (not shown) determines that a vertical direction eye movement has been performed when the respective potentials of the first electrode 152 and the second electrode 154 based on the inter-brow third electrode 156 are in phase and the peak width is not within a predetermined period (0.25 seconds, for example). More specifically, the eye movement determination unit determines that the eyes have moved upward when the potential of the first electrode 152 and the potential of the second electrode 154 are negative, and determines that the eyes have moved downward when the potential of the first electrode 152 and the potential of the second electrode 154 are positive.

Note that in this embodiment, a case in which the eyewear is constituted by spectacles was described, but the eyewear is not limited thereto, and may be any eye-related accoutrement, for example face-mounted equipment or head-mounted equipment such as spectacles, sunglasses, goggles, or a head-mounted display, as well as a frame thereof.

In this embodiment, an example in which the spectacles 100 include the third electrode 156 was described, but the spectacles 100 are not limited thereto, and do not have to include the third electrode 156. In this case, an electrooculogram showing the potential of the first electrode 152 based on a reference electrode and an electrooculogram showing the potential of the second electrode 154 based on the reference electrode may be transmitted to the external device 300. Here, a ground electrode may be provided in the position of the third electrode 156 and used as the reference electrode. Alternatively, the ground electrode provided on the left temple tip may be used as the reference electrode, or an electrode provided separately in a position away from the first electrode 152 and the second electrode 154 may be used as the reference electrode.

In this embodiment, an example in which the spectacles 100 include the nose pads 140 formed integrally with the rims 122 was described, but the spectacles 100 are not limited thereto, and may include clips mounted on the rims 122 and nose pads 140 attached to the clips. In this case, the electrodes provided on the respective surfaces of the nose pads 140 are electrically connected to the electrical wires embedded in the frame via the clips.

In this embodiment, an example in which the first electrode 152 and the second electrode 154 are provided on the lower side of the center of the nose pads 140 was described, but the present invention is not limited thereto, and instead, the nose pads 140 may respectively include extension portions that extend toward the lower side, and the first electrode 152 and the second electrode 154 may be provided on the respective extension portions. As a result, the first electrode 152 and the second electrode 154 can be brought into contact with positions below the eyes of the user in a case where, due to individual differences in the positions of the eyes and nose, the nose pads are positioned directly alongside the eyes.

In this embodiment, an example in which the third electrode 156 is provided on the surface of the inter-brow portion 124 was described, but the present invention is not limited thereto, and instead, the inter-brow portion 124 may include an extension portion that extends toward the upper side, and the third electrode 156 may be provided on the extension portion. Further, a movable portion capable of moving the extension portion vertically may be provided between the extension portion and the inter-brow portion 124 so that the position of the third electrode 156 can be adjusted vertically. As a result, the contact position of the third electrode 156 can be adjusted away from the eyes of the user in a case where, due to individual differences in the positions of the eyes, the contact position of the third electrode 156 is close to the eyes. Moreover, in this embodiment, the positions of the respective electrodes are not limited to the positions described above, and the electrodes may be disposed in any positions where eye potential signals indicating vertical direction and horizontal direction eye movements can be acquired.

In this embodiment, eye potential signals were used as examples, but the processing may be executed using a difference signal or an extreme value difference signal of an eye potential signal. A difference signal is a signal representing a difference between a predetermined eye potential signal and an eye potential signal acquired a predetermined time before the predetermined eye potential signal. The predetermined time is set at 5 msec or the like, for example. By obtaining the signal difference, noise resistance can be strengthened. Note that obtaining the difference between these signals is synonymous with implementing differentiation.

An extreme value difference signal is a signal representing a difference between adjacent extreme values (peak values) of an eye potential signal or a difference signal. By obtaining the extreme value difference signal, an eye movement or the like can be determined appropriately without being affected by a signal level or the like immediately before the eye movement.

In this embodiment, any biological signal acquired by quantifying a biological phenomenon such as pulse, heart rate, brain waves, respiration, or perspiration using a sensor may be applied. Furthermore, this embodiment is not limited to a biological signal, and any signal that has a peak when a predetermined event occurs may be applied.

In this embodiment, a separate device to the processing device 200, for example a personal computer or a portable communication terminal such as a mobile telephone or a smartphone carried by the user, was cited as an example of the external device 300, but the present invention is not limited thereto, and the external device 300 may be a unit formed integrally with the processing device 200. In this case, the external device 300 is provided integrally with the eyewear. Further, the functions of any of the parts of the external device 300 may be incorporated into the processing device 200.

Furthermore, in this embodiment, noise intermixing may be prevented by employing shielded cable as the electrical wires.

Further, in this embodiment, FIG. 1 shows an example configuration in which three electrodes are used, but four or more electrodes may be used. In this case, the spectacles include an upper portion electrode, a lower portion electrode, a left portion electrode, and a right portion electrode. For example, the upper portion electrode and the lower portion electrode are provided on the rims 122 shown in FIG. 1, while the left portion electrode is provided on the left temple 130 and the right portion electrode is provided on the right temple 130. Note, however, that the electrodes do not necessarily have to be provided in these positions. It is assumed that the electrodes contact parts of the face. Furthermore, the spectacles may be configured such that two electrodes are provided in the respective positions of the first electrode 152, the second electrode 154, and the third electrode 156.

In an example in which four electrodes are provided, the vertical direction of the eyes can be detected from a voltage difference between the upper portion electrode and the lower portion electrode, and the left-right direction of the eyes can be detected from a voltage difference between the left portion electrode and the right portion electrode.

The present invention was described above using an embodiment, but the technical scope of the present invention is not limited to the scope of the above embodiment, and it will be obvious to a person skilled in the art that various amendments and improvements may be added to the above embodiment. It is obvious from the description of the claims that embodiments acquired by adding such modifications or improvements are also included in the technical scope of the present invention.

REFERENCE SIGNS LIST

100 Spectacles
120 Frame
124 Inter-brow portion
140 Nose pad
152 First electrode
154 Second electrode
156 Third electrode
200 Processing device
300 External device
320 Storage unit
330 Control unit
332 Acquisition unit
334 Detection unit
336 Attachment unit
338 Extraction unit
340 Reception unit
342 Specification unit

What is claimed is:

1. An information processing method executed by a computer having a processor, wherein the processor executes:

acquiring a plurality of biological signals respectively from a plurality of sensors on an eyewear;

sampling the plurality of biological signals at a predetermined sampling interval to obtain a plurality of signal values;

detecting at least one signal value as a peak part among the plurality of signal values;

providing identification information to each of the at least one signal value detected as the peak part respectively for each biological signal of the plurality of biological signals; and after the identification information is respectively provided to at least two signal values obtained by sampling at a sampling timing of at least two biological signals of the plurality of biological signals, determining the identification information provided to the at least two signal values as being based on an identical event.

2. The information processing method according to claim 1, wherein the detecting includes detecting the at least one signal value as the peak part when the at least one signal value is not lower than a first threshold and not higher than a second threshold, and the providing includes providing, for each of the plurality of biological signals, identical identification information to a plurality of signal values among the at least one signal value that are consecutively not lower than the first threshold and not higher than the second threshold.

3. The information processing method according to claim 1, wherein the at least two biological signals are chosen arbitrarily.

4. The information processing method according to claim 1, wherein the processor further executes specifying one first biological signal from among the at least two biological signals, and the determining the identification information provided to the at least two signal values as being based on an identical event includes associating the identification information provided to the signal values obtained by sampling at a timing of the first biological signal.

5. The information processing method according to claim 4, wherein the determining the identification information provided to the at least two signal values as being based on an identical event includes determining the at least two signal values as being based on the identical event.

6. An information processing device comprising a processor, wherein the processor is configured to execute to:

acquiring a plurality of biological signals respectively from a plurality of sensors on an eyewear;

sampling the plurality of biological signals at a predetermined sampling interval to obtain a plurality of signal values;

detecting at least one signal value as a peak part among the plurality of signal values;

providing identification information to each of the at least one signal value detected as the peak part respectively for each of the plurality of biological signals; and after the identification information is respectively provided to at least two signal values obtained by sampling at a sampling timing of at least two biological signals of the plurality of biological signals, determining the identification information provided to the at least two signal values as being based on an identical event.

7. A computer-readable non-transitory recording medium comprising a program configured to cause a computer to execute:

acquiring a plurality of biological signals respectively from a plurality of sensors on an eyewear;

sampling the plurality of biological signals at a predetermined sampling interval to obtain a plurality of signal values;

detecting at least one signal value as a peak part among the plurality of signal values;
providing identification information to each of the at least one signal value detected as the peak part respectively for each of the plurality of biological signals; and
after the identification information is respectively provided to at least two signal values obtained by sampling at a sampling timing of at least two biological signals of the plurality of biological signals, determining the identification information provided to the at least two signal values as being based on an identical event.

8. Eyewear comprising:
a frame;
a pair of nose pads provided on the frame;
electrodes provided respectively on the pair of nose pads;
an acceleration sensor or an angular velocity sensor provided on the frame; and
a processor, wherein the processor is configured to execute to:
acquiring biological signals respectively from the electrodes and the acceleration sensor or angular velocity sensor;
sampling the plurality of biological signals at a predetermined sampling interval to obtain a plurality of signal values;
detecting at least one signal value as a peak part among the plurality of signal values;
providing identification information to each of the at least one signal value detected as the peak part respectively for each of the plurality of biological signals; and
after the identification information is respectively provided to at least two signal values obtained by sampling at a sampling timing of at least two biological signals of the plurality of biological signals, determining the identification information provided to the at least two signal values as being based on an identical event.

* * * * *